United States Patent
Kovacs et al.

[19]

[11] Patent Number: 5,941,856
[45] Date of Patent: Aug. 24, 1999

[54] MEDICAL CONDUIT HOLDER WITH STABILIZING MEMBER

[75] Inventors: Joseph L. Kovacs, Cranston, R.I.; Irving Forman, Framingham, Mass.

[73] Assignee: Dale Medical Products, Inc., Plainville, Mass.

[21] Appl. No.: 08/936,402

[22] Filed: Sep. 25, 1997

[51] Int. Cl.[6] ................................... A61M 25/02
[52] U.S. Cl. .................................. 604/179; 128/DIG. 26
[58] Field of Search ..................... 604/174, 179, 604/180, 293, 308, 392, 391; 602/79; 128/DIG. 26

[56] References Cited

U.S. PATENT DOCUMENTS

| | | | |
|---|---|---|---|
| 4,445,894 | 5/1984 | Kovacs | 604/179 |
| 4,671,787 | 6/1987 | Widman | 604/179 |
| 4,838,878 | 6/1989 | Kalt et al. | 604/180 |
| 5,037,397 | 8/1991 | Kalt et al. | 604/174 |
| 5,048,512 | 9/1991 | Turner et al. | 604/179 |
| 5,098,399 | 3/1992 | Tollini | 604/180 |
| 5,403,285 | 4/1995 | Roberts | 604/179 |
| 5,496,282 | 3/1996 | Millitzer et al. | 604/179 |
| 5,549,567 | 8/1996 | Wolman | 604/179 |
| 5,664,581 | 9/1997 | Ashley | 604/179 |

*Primary Examiner*—Wynn Wood Coggins
*Assistant Examiner*—Sharon Finkel
*Attorney, Agent, or Firm*—Wolf, Greenfield & Sacks, P.C.

[57] ABSTRACT

A medical conduit holder for releasably securing and reattaching a medical conduit, for example, a Foley catheter, to the limb of a patient. The holder includes a non-stretchable stabilizing member having a looped fabric surface, and attached to a stretchable primary strap to form an enclosed nonstretchable area of the primary strap. The primary strap is configured for attachment to the limb of the patient. The holder further includes a secondary strap attached to both the platform and the primary strap, preferably at the center of the secondary strap. The secondary strap has a first portion with a window, and an engagement portion dimensioned to loop around the conduit and fit through the window. In use, the engagement portion is looped over the medical conduit and through the window, such that the hooked surface of the engagement portion contacts the looped surface of the stabilizing member in order to secure the medical conduit. The first portion is then likewise looped over the medical conduit, such that the hooked surface of the first portion contacts the looped fabric surface of the platform. The stabilizing member resists buckling in order to retain the medical conduit in place, with little movement of the conduit relative to the primary strap.

11 Claims, 4 Drawing Sheets

MEDICAL CONDUIT HOLDER WITH STABILIZING MEMBER

TECHNICAL FIELD

The present application relates to a medical conduit holder, and more particularly to a medical conduit holder, including a stabilizing member, for releasably securing catheters and similar devices to the limb of a patient.

BACKGROUND OF RELATED ART

A number of devices are known for securing medical conduits to the limb of a patient. These devices typically include a primary strap which is adjustably secured around the limb of a patient, and a secondary strap, attached to the primary strap, which engages and secures the medical conduit in place.

One often-performed medical procedure requiring the use of a medical conduit holder is trans-urethral resection of the prostate (TURP), which is performed to relieve lower urinary tract obstructions. During the TURP procedure, a large Foley catheter with a 30-mL (milliliter) balloon is placed in the urethra to tamponade the surgical area and to drain the bladder. Active bleeding from the vascular prostatic tissue may continue for 24 to 48 hours, requiring continuous or intermittent irrigation to maintain catheter patency (flow). It can, therefore, be appreciated that catheter stability in such a procedure is very important, as movement or pulling of the catheter may cause the balloon to dislodge and block the flow of blood from the bladder. Other procedures, such as the Radical Perineal Prostatectomy (RPP), may require a Foley catheter to remain in place within the bladder for two weeks, or more, with little or no movement of the catheter until removal from the patient.

One commercially-successful device utilized to secure a conduit, such as a Foley catheter, is disclosed in U.S. Pat. No. 4,445,894 to Kovacs ('894 patent). The device includes a primary strap which is configured to be fastened around a limb of a patient, and a secondary strap which secures the medical conduit in place. The primary strap includes a stretchable section and a non-stretchable section having Velcro™-type loops. The secondary strap has Velcro™-type hooks for attachment to the non-stretchable looped section of the primary strap. The secondary strap may be a single piece of material which is sewn at an angle with respect to the primary strap. The secondary strap is sewn transversely down the center, so as to divide it in half, with the hooked surfaces of the two halves facing upwardly, away from the looped surface of the primary strap. The two halves of the secondary strap (on opposite sides of the stitching) are adapted to be looped over the medical conduit and hold the conduit in place by engagement of the hooks of the secondary strap with the looped fabric of the primary strap (FIG. 1a). Alternately, the '894 patent discloses that the secondary strap may include two straps made of hooked, Velcro™-type material, which are each approximately half the size of the single, secondary strap. When utilizing two half-straps, the two halves are each secured parallel to the primary strap and offset from each other, each strap being stitched to the primary strap along its inner edge (FIG. 1b). The two, separate halves of the secondary strap may then be looped over the medical conduit in the same fashion as described with respect to the single, secondary strap.

FIG. 1c illustrates another prior art device for securing medical conduits, such as Foley catheters, to a limb. This device has been sold by Dale Medical Products, Inc. of Plainville, Mass., under the name "Foley Catheter Holder", and product number 316. The device (110) illustrated in FIG. 1c includes a primary strap (116) made of a stretchable fabric and a rectangular base piece (136) of non-stretchable fabric having a looped surface, which is sewn to the primary strap. The piece (136) is sewn in the transverse (width direction) to the primary strap (116) along its two opposing short ends, and also in the middle, parallel to the two opposing short ends. The device further includes a secondary strap (118) made of non-stretchable, hooked, Velcro™-type plastic material. The secondary strap includes a first rectangular portion (142) having an aperture (144) formed therethrough, and a second, elongated engagement portion (146) formed integrally with and narrower in width than the first portion. To attach the secondary strap to the platform, a transverse stitch (width direction) is sewn through the secondary strap, between the window and the engagement portion, such that the hooked surface of the secondary strap faces upwardly, away from the looped fabric surface of the platform. The secondary strap may alternatively/additionally be attached to the primary strap by stitching, so as to attach the center of the base piece to the primary strap. In use, the medical conduit is placed on the secondary strap, between the window and the engagement portion, adjacent the stitching. The engagement portion is then looped over the medical conduit and through the window of the secondary strap, such that the hooked surface of the engagement portion contacts the looped fabric surface of the platform in order to secure the engagement portion to the platform. The first rectangular portion is then likewise looped over the medical conduit, such that the hooked surface of the rectangular portion contacts the looped fabric surface of the base piece. The base piece may somewhat limit the lengthwise stretchability of the primary strap along the side edges where the base piece is sewn, but does not eliminate the lengthwise stretchability under the base piece where the base piece is not sewn.

Although the aforementioned prior art devices have been successfully used to secure a catheter to the limb of a patient, in certain circumstances the catheter may become loose, especially if the primary strap is repositioned on the patient. For example, repositioning of Dale's 316 device described above, may cause buckling of the base piece (FIG. 1c), resulting in movement of the catheter. In certain procedures, such as TURP, any movement is undesirable.

There is therefore a need for a device which will very securely hold a medical conduit, such as a Foley catheter, in position on the patient, even after repositioning of the device.

SUMMARY

In accordance with the present invention, a medical conduit holder is provided for removably securing a medical conduit to the limb of a patient. The holder includes a non-stretchable stabilizing member attached around its perimeter to enclose an area of a stretchable, primary strap (attached to the patient's limb), and render the enclosed area non-stretchable. The holder further includes a secondary strap, or locking strip, which is stitched to both the platform and the primary strap, at approximately the center of the secondary strap. The secondary strap includes a first portion having a window disposed therethrough, and an engagement portion dimensioned to fit within the window. The secondary strap may be made of a male, Velcro™-type material with hook-like protrusions. In use, the engagement portion is looped over the medical conduit and through the window, such that the hooked surface of the engagement portion contacts a looped surface of the stabilizing member in order to secure the medical conduit. The first portion is likewise looped over the medical conduit, such that the hooked surface (of the first portion) contacts the looped surface (of the platform) to further secure the engagement portion to the stabilizing member. By securing the stabilizing member along its perimeter, the stabilizing member resists buckling and the primary strap resists movement, in order to retain the medical conduit in place, with little movement of the conduit relative to the primary strap.

These and other features and benefits of the present invention will be more particularly described in the following detailed description and drawings.

BRIEF DESCRIPTION OF THE DRAWINGS

FIG. 1b is a top view of a second embodiment of the conduit holder of FIG. 1a;

DETAILED DESCRIPTION OF THE ILLUSTRATIVE EMBODIMENTS

Figure 1A:
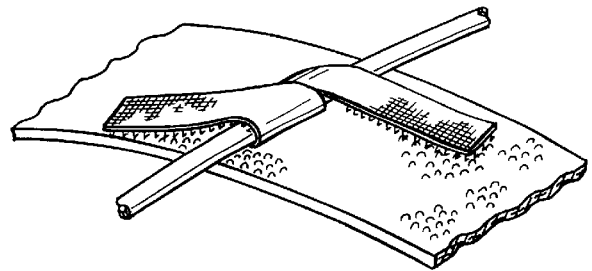
FIG. 1a is a perspective view of a prior art conduit holder engaging a medical conduit.
Figure 1B:
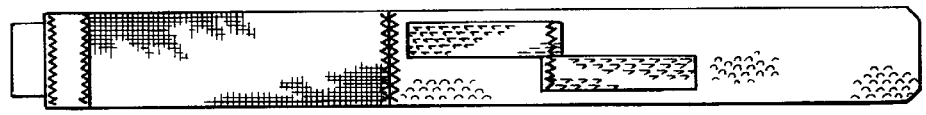
Figure 1C:
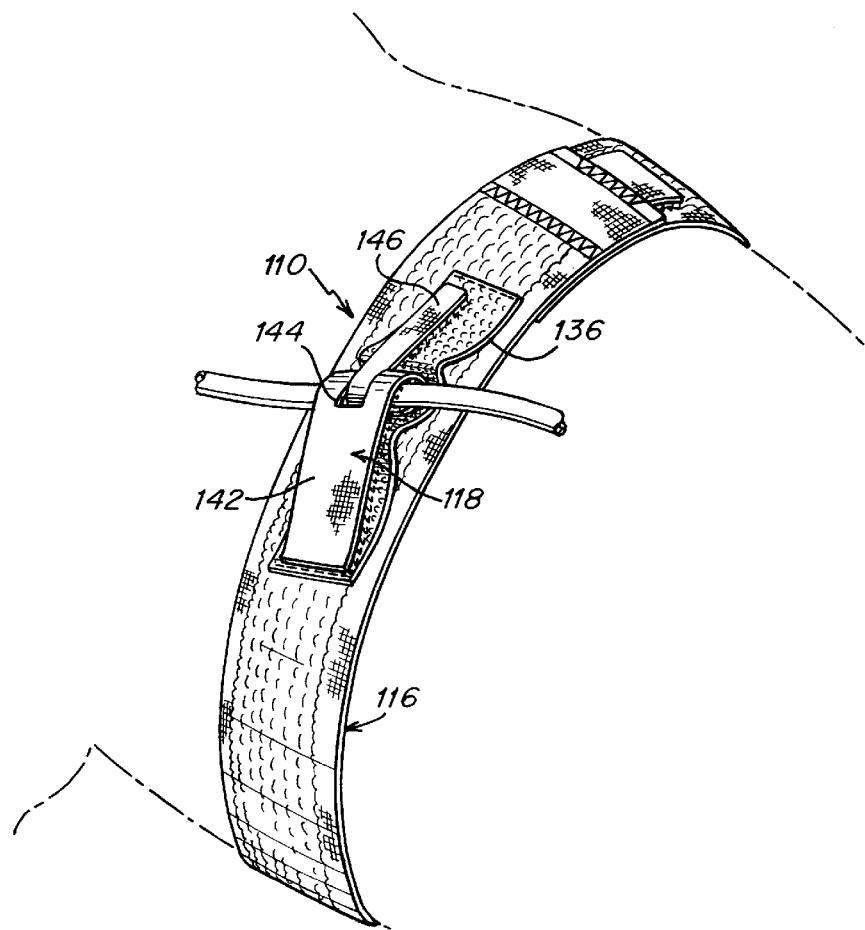
FIG. 1c is a perspective view of a prior art conduit holder attached to a leg of a patient.
Figure 2:
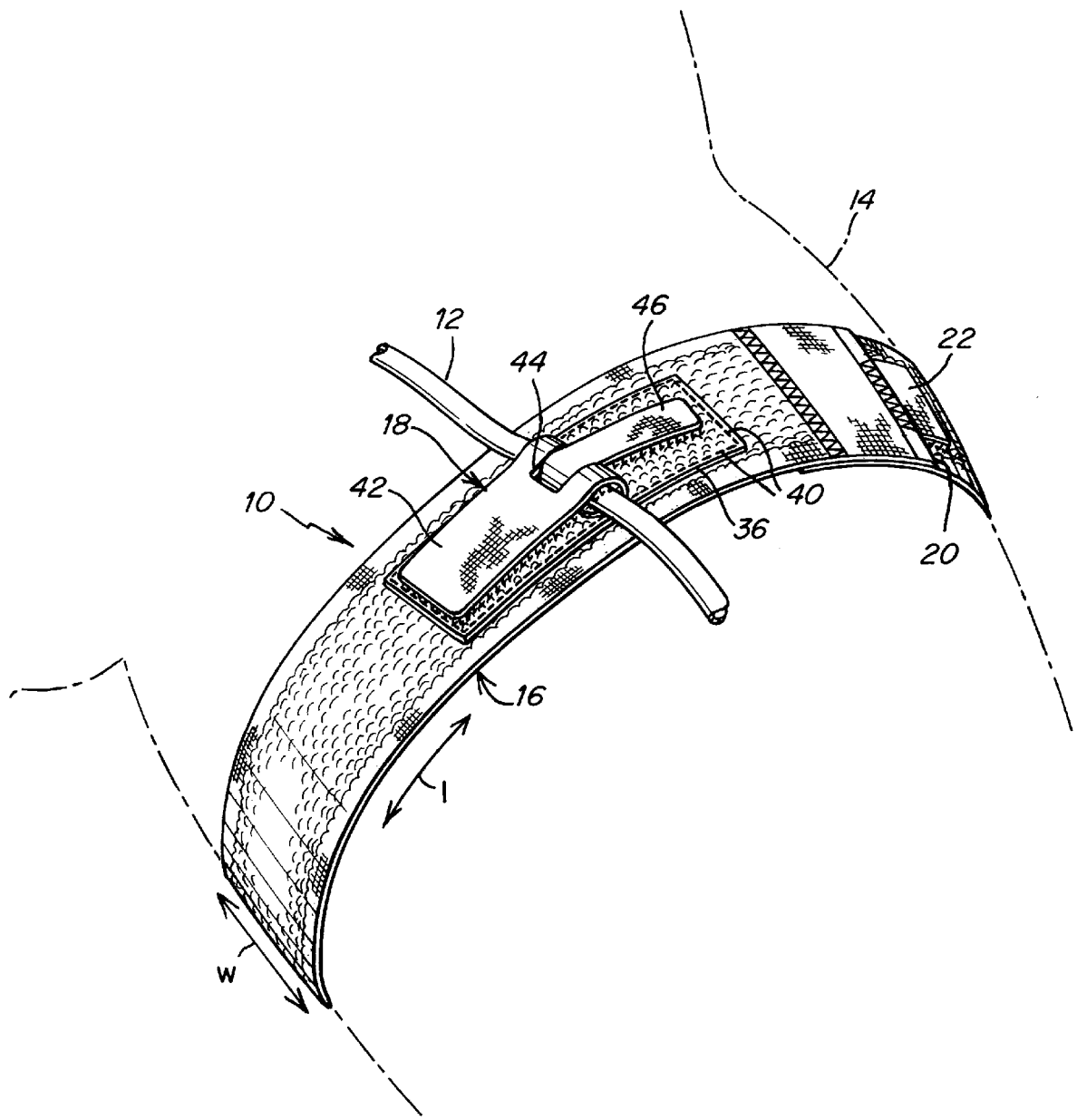
FIG. 2 is a perspective view of one embodiment of a conduit holder attached to a leg of a patient, according to the present invention.

A medical conduit holder 10 for securing a medical conduit 12, for example a Foley catheter, to the limb of a patient 14 is illustrated in FIG. 2. The holder 10 includes a primary strap 16 which is configured to wrap around a limb of a patient, and a locking or secondary strap 18 which engages the medical conduit 12 to hold it securely in position relative to primary strap 16. The primary strap is preferably made of a stretchable material, such as an elastic webbing, which is stretchable in a lengthwise ("l") direction, but is of a relatively fixed dimension across its width ("w"). The primary strap (FIG. 3) also includes a first end 20 having a fastening member 22 extending therefrom, and a second end 24, opposite the first end. In the present embodiment, the primary strap 16 is approximately 19.5 inches in length, in an unstretched configuration, and 2 inches in width, so as to be readily adjustable in order to comfortably fit a majority of adult patients; other dimensions are contemplated, for example for pediatric use.

Figure 5:
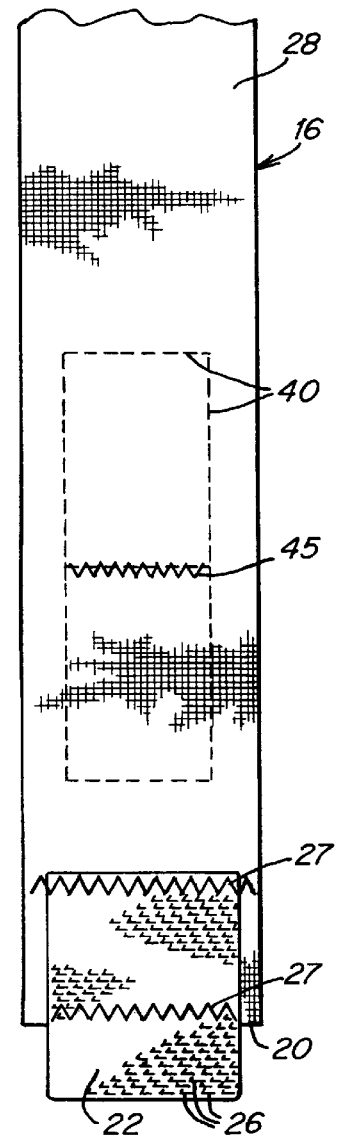
FIG. 5 is an enlarged bottom view of the conduit holder of FIG. 4 showing the stitching of the stabilizing platform.

The fastening member 22 may be made from a piece of non-stretchable male Velcro™-type fastening material having hook-like protrusions 26 on one side thereof (FIG. 5), or may be any other type of fastener capable of adjustably securing the primary strap 16 about the limb of the patient. The fastening member 22 may be stitched 27 to an inner surface 28 of the primary strap, with the hook-like protrusions 26 facing away from the inner surface as shown in FIG. 5. By attaching the fastening member 22 in this manner, the hook-like protrusions 26 will engage the exterior surface 30 of the primary strap when the primary strap is wrapped around the limb of the patient, thereby releasably securing the first end 20 of the primary strap 16. In the present embodiment, the fastening member 22 is approximately 2 inches long, and 1 ⅜ inches wide, although other dimensions are contemplated, as would be apparent to one of skill in the art.

Figure 3:
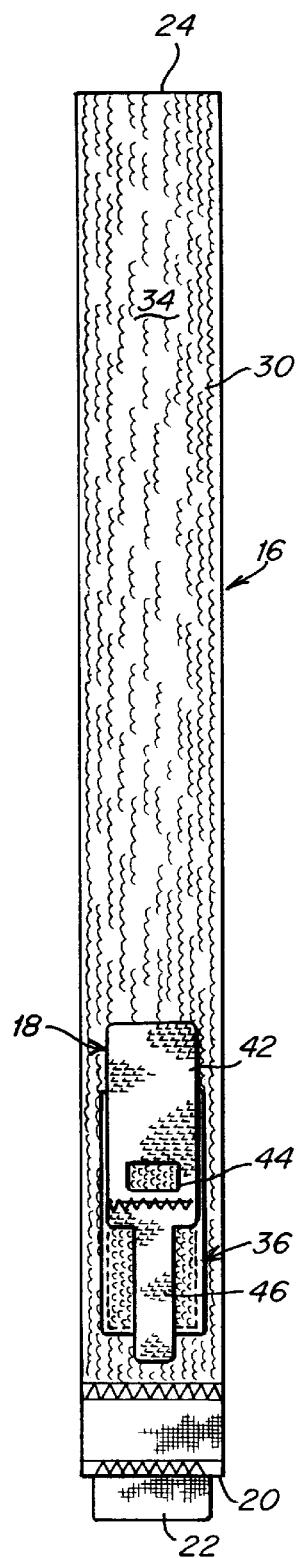
FIG. 3 is top view of the conduit holder of FIG. 2 in an open, non-engaged configuration.
Figure 4:
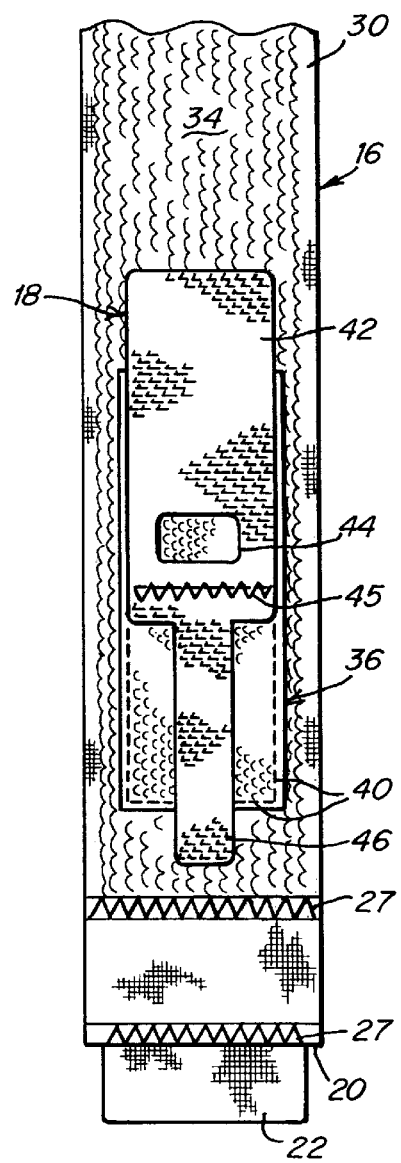
FIG. 4 is an enlarged top view of the conduit holder of FIG. 3 showing a secondary strap attached to a stabilizing platform.

As shown in FIG. 2, the inner surface 28 of the primary strap 16 lies against the skin of the patient when the strap 16 is in place about the limb. The inner surface 28, therefore, preferably includes a soft lining or backing material which feels comfortable when contacting the skin, but which preferably does not interfere with the elasticity of the webbing of the primary strap. The exterior surface 30 of the primary strap 16 is preferably made of a looped fabric 34, for example cotton, disposed along at least a portion of the length of the primary strap in order to facilitate connection of the male Velcro-type fastening member 22 to the exterior surface 30. As shown in FIG. 3, the looped fabric may extend along substantially the entire length of the primary strap in order to give a wide range of sizing options, provided that the looped fabric does not interfere with the elasticity of the webbing of the primary strap. In the present embodiment, the primary strap is preferably made of a combination of textured polyester yarn, stretch nylon and lycra/spandex material, available from DuPont de Nemours, E.I., Co, Wilmington, Del., product number V21L. The combination of polyester and stretch nylon produces an ultra soft plush effect for the inner surface which insures comfort (against the skin), while the opposite side is Velcro compatible.

The exterior surface 30 (FIG. 4) also preferably includes a stabilizing member 36 secured thereto, the stabilizing member providing a stationary platform against which the secondary strap 18 is secured. Stabilizing member 36 is preferably secured to the stretchable primary strap 16 in such a manner so as to substantially eliminate the stretchability of the primary strap in area ("A"), which is the area of the primary strap under or enclosed by the stabilizing member. In the present embodiment, this is accomplished by utilizing a piece of non-stretchable, plastic material with a pile of fabric loop on one side thereof. Such plastic material 36 is the type commonly utilized to mate with hook-shaped protrusions to form a Velcro™-style fastener. To substantially eliminate the undesirable stretchability in the area which will support the medical conduit, the stabilizing member 36 is first formed, such as by cutting, into an appropriate shape and size to support the secondary strap 18. In order to limit the stretchability of the primary strap 16 along that portion (of the primary strap) beneath the stabilizing member, the stabilizing member is attached to the primary strap in a manner which renders it stationary relative to the primary strap, even during positioning and adjustment of the primary strap. There is, therefore, no relative movement between the stabilizing member 36 and area "A" of the primary strap. This preferably is accomplished by securing the stabilizing member 36 substantially along its entire perimeter to the primary strap 16. In the present embodiment, the stabilizing member 36 is sewn along its perimeter, which substantially eliminates the stretchability of the primary strap in the area "A." A simple straight stitch 40 may be used, to secure the stabilizing member, although other stitches may be used, as would be known to one of skill in the art. In the embodiment of FIGS. 2–5, the stabilizing member 36 is rectangular in shape, with an overall length of approximately 3 11/16ths of an inch, and an overall width of approximately 1 inch. It should be appreciated that alternate shapes and sizes may be utilized. Stabilizing member 36 is also preferably attached to the primary strap with the pile fabric loop facing upward so that secondary strap 18 can engage the fabric loop as discussed below.

Secured to the stabilizing member 36 is secondary strap 18. Secondary strap 18 preferably includes a first rectangular portion 42 having a therethrough, and a second, elongated engagement portion 46 which is preferably formed as an integral member with the first portion and preferably sized so as to be insertable within window 44. To attach the secondary strap to the stabilizing member a transverse (width direction) stitch 45, such as a bar-tack stitch, is sewn through the secondary strap, between the window 44 and the engagement portion 46; the stitch 45 also connects the center of the stabilizing member 36 to the primary strap. In the present embodiment, the transverse stitch 45 is sewn approximately 4 ¼ inches from end 20 of the primary strap. The secondary strap is preferably formed of non-stretchable, hooked, Velcro™-type plastic material and is attached to the stabilizing member 36 such that the hooked surfaces of the secondary strap faces upwardly and away from the fabric loop of the stabilizing member. The overall length of the secondary strap is approximately 5 5/16 inches, and the window 44 has an opening measuring approximately 0.56 inches long by 0.44 inches wide. In the present embodiment, the engagement portion 46 has a length of approximately 2 ½ inches and a width of approximately 0.5 inches, while the rectangular portion 42 has a length of approximately 3 inches and a width of approximately 1 inch. The secondary strap may have rounded edges to avoid sharp corners which may cut the patient and/or nurse. The configuration, size and shape of the secondary strap may be varied, provided that the secondary strap is secured to the stabilizing member.

Figure 6:
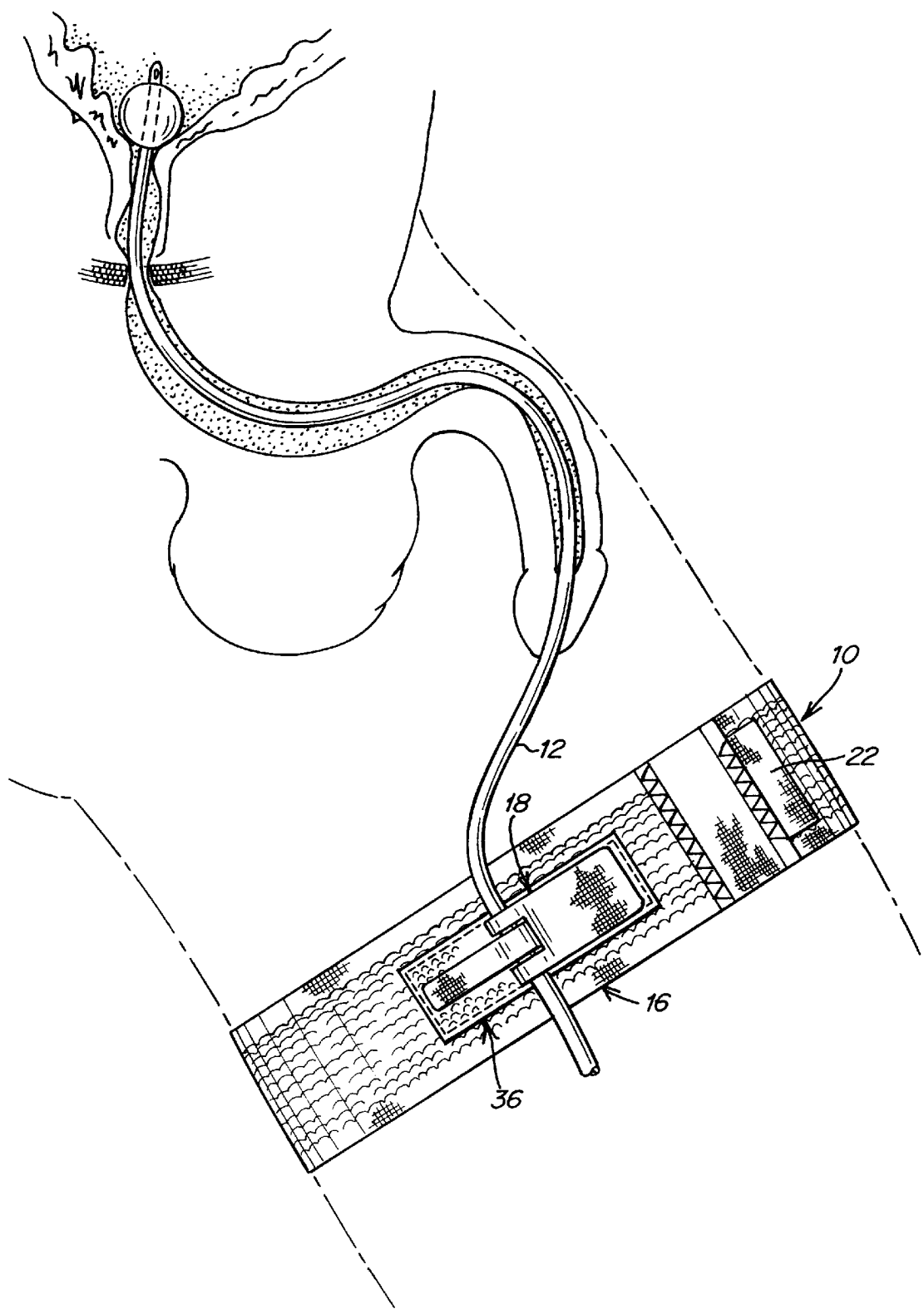
FIG. 6 is a schematic illustrating the conduit holder of FIG. 1 in use after an illustrative procedure.

FIG. 6 illustrates use of the holder 10 during a TURP procedure, wherein the medical conduit 12 is placed on the secondary strap, between the window 44 and the engagement portion 46, adjacent the transverse stitching 45. The engagement portion 46 is then looped over the medical conduit and is inserted through the window of the secondary strap, such that the hooked surface of the engagement portion contacts the looped fabric surface of the stabilizing member. The rectangular portion 42 of the secondary strap is then likewise looped over the medical conduit 12, such that the hooked surface of the rectangular portion contacts the looped fabric surface of the stabilizing member. Because the stabilizing member 36 is secured along its perimeter, it resists buckling and the primary strap 16 resists movement when the medical conduit is secured by the secondary strap, thereby retaining the medical conduit in place, with little movement of the conduit relative to the primary strap.

It will be understood that various modifications may be made to the embodiment disclosed herein. For example, the secondary strap may have a variety of configurations for securing the medical conduit, provided the secondary strap is secured to a stabilizing member to resist buckling. Therefore, the above description should not be construed as limiting, but merely as an exemplification of a preferred embodiment. Those skilled in the art will envision other modifications within the scope the invention.

We claim:

1. A medical conduit holder for securing a medical conduit to a limb of a patient comprising:
    a primary strap stretchable in at least a lengthwise direction extending between first and second ends of the primary strap;
    a fastening member supported by the primary strap for releasably securing the primary strap about the limb of the patient;
    a stabilizing member secured to the primary strap substantially along an entire perimeter of the stabilizing member to define an enclosed area of the primary strap which is nonstretchable in at least the lengthwise direction; and
    a secondary strap attached to the stabilizing member and having first and second ends adapted to releasably engage the stabilizing member and secure the medical conduit perpendicular to the lengthwise direction of the primary strap, wherein the first and second ends of the secondary strap each exert a pulling force on the stabilizing member when the first and second ends engage the stabilizing member and secure the medical conduit, respectively, the pulling forces from the first and second ends tending to pull the stabilizing member away from the primary strap so that securing the stabilizing member along its entire perimeter prevents the stabilizing member from separating from the primary strap due to the pulling forces from the first and second ends of the secondary strap.

2. The medical conduit holder of claim 1, wherein the stabilizing member is secured in the lengthwise direction to the primary strap.

3. The medical conduit holder of claim 1, wherein the stabilizing member is sewn to the primary strap.

4. The medical conduit holder of claim 1, wherein the stabilizing member is rectangular and its elongated edges are secured in the lengthwise direction to the primary strap.

5. The medical conduit holder of claim 2, wherein the stabilizing member is a non-stretchable piece of plastic having a pile of fabric loop on one side thereof.

6. The medical conduit holder of claim 1, wherein the secondary strap has a first portion with a window formed therethrough, and a second elongated engagement portion.

7. The medical conduit holder of claim 6, wherein the engagement portion is insertable within the window while looped over the medical conduit.

8. The medical conduit holder of claim 1, wherein the secondary strap is secured to the stabilizing member and the primary strap.

9. The medical conduit holder of claim 1, wherein the secondary strap is nonstretchable.

10. The medical conduit holder of claim 1, wherein the enclosed area is substantially nonstretchable in a transverse direction.

11. The medical conduit holder of claim 1, wherein the pulling forces of the first and second ends oppose one another.

* * * * *